(12) United States Patent
Tate et al.

(10) Patent No.: US 8,517,723 B2
(45) Date of Patent: Aug. 27, 2013

(54) METHODS FOR DRYING A VIRAL VACCINE

(75) Inventors: Jeffrey L. Tate, North Port, FL (US);
David A. Mirko, Payson, AZ (US);
James A. Rehkopf, San Rafael, CA (US)

(73) Assignee: Pulse Holdings, LLC, Payson, AZ (US)

( * ) Notice: Subject to any disclaimer, the term of this patent is extended or adjusted under 35 U.S.C. 154(b) by 786 days.

(21) Appl. No.: 12/243,435

(22) Filed: Oct. 1, 2008

(65) Prior Publication Data
US 2009/0087452 A1 Apr. 2, 2009

Related U.S. Application Data

(60) Provisional application No. 60/997,337, filed on Oct. 1, 2007.

(51) Int. Cl.
*F23L 15/04* (2006.01)
*A61K 39/12* (2006.01)
*C12Q 1/70* (2006.01)

(52) U.S. Cl.
USPC ................... 432/29; 424/204.1; 435/5

(58) Field of Classification Search
None
See application file for complete search history.

(56) References Cited

U.S. PATENT DOCUMENTS

| | | |
|---|---|---|
| 5,026,566 A | 6/1991 | Roser |
| 5,209,821 A | 5/1993 | Shaw et al. |
| 6,763,607 B2 | 7/2004 | Beyerinck et al. |
| 7,244,825 B2 | 7/2007 | Roser |

FOREIGN PATENT DOCUMENTS

JP 2006-197829 8/2006

OTHER PUBLICATIONS

Elhafi et al., Microwave or autoclave treatments destroy the infectivity of infectious bronchitis virus and avian pneumovirus but allow detection by reverse transcriptase-polymerase chain reaction, 2010, Avian Pathology, vol. 33, No. 3, pp. 303-306.*
CDC, Guideline for Disinfection and Sterlization in Healthcare Facilities, 2008.*
Maa et al., Stabilization of Alum-Adjuvanted Vaccine Dry Powder Formulations: Mechanism and Application, 2002, Journal of Pharmaceutical Sciences, vol. 92, No. 2, pp. 319-332.*
Wang, Liang, et al., Improvement of the Dissolution Rate of Nitrendipine Using a New Pulse Combustion Drying Method, Chem. Pharm. Bull., Aug. 2007, pp. 1119-1125, vol. 55, No. 8.
Xu, Lu, et al., Preparation and Evaluation of Ibuprofen Solid Dispersion Systems with Kollidon Particles Using a Pusle Combustion Dryer System, Chem. Pharm. Bull., Nov. 2007, pp. 1545-1550, vol. 55, No. 11.
Zbicinski, Ireneusz, et al., Pulse Combustion: An Advanced Technology for Efficient Drying, Chemical Engineering and Technology, 2002, pp. 687-691, vol. 25.

* cited by examiner

*Primary Examiner* — Benjamin P Blumel
(74) *Attorney, Agent, or Firm* — Benjamin C. Armitage; Billion & Armitage

(57) ABSTRACT

A viral vaccine in the dried state is described. Methods for drying viral vaccine in the liquid state into viral vaccine in the dried state are presented. The methods may include introducing the viral vaccine in the liquid state into a gas stream and recovering viral vaccine in the dried state from the gas stream.

15 Claims, 3 Drawing Sheets

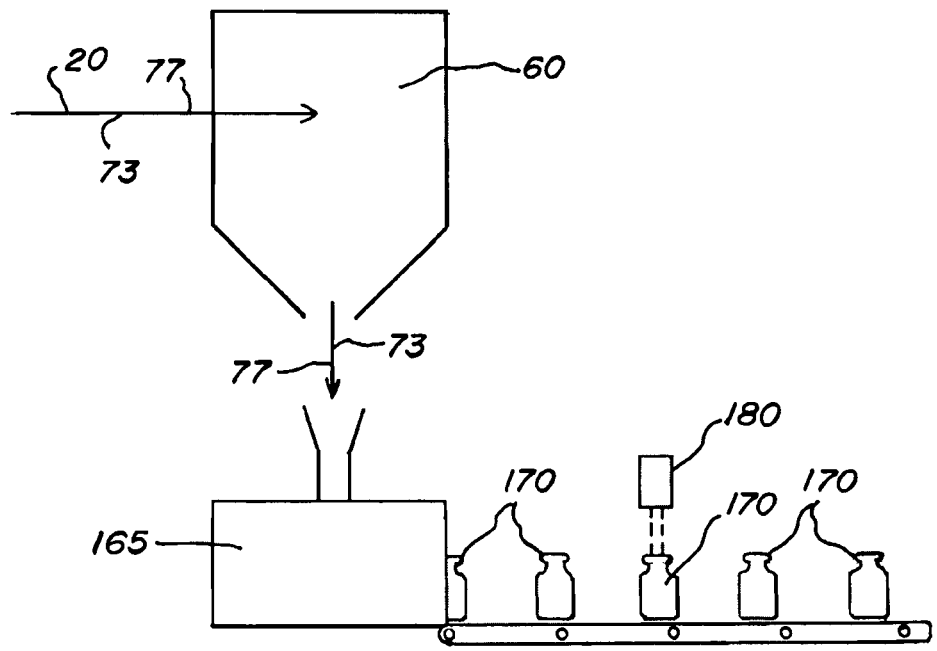
Figure 3A
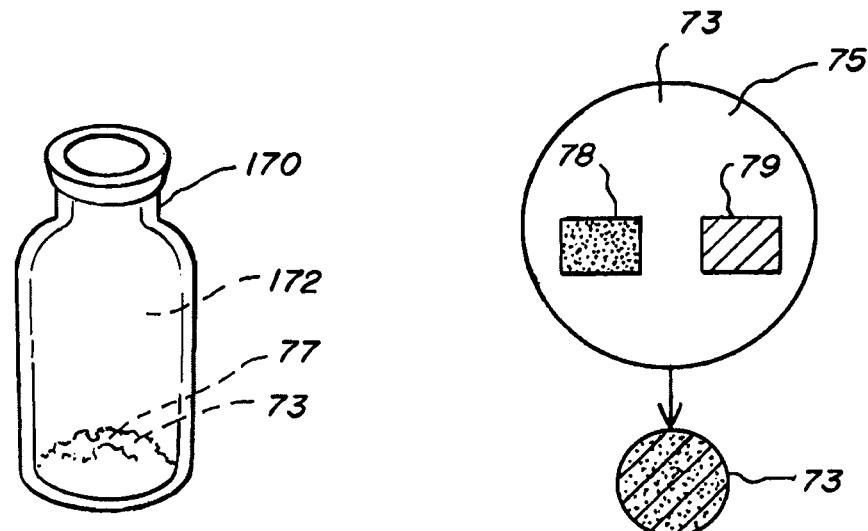
Figure 3B
Figure 4

METHODS FOR DRYING A VIRAL VACCINE

PRIORITY

This application claims the benefit of U.S. Provisional application No. 60/997,337 filed on Oct. 1, 2007 which is incorporated herein by reference in its entirety.

FIELD OF THE INVENTION

The present inventions relate to viral vaccines and, in particular, to methods and apparatus for the production of dried viral vaccines.

BACKGROUND OF THE INVENTION

Viruses are the source of diseases and other health issues faced by the world's human and animal populations. A wide variety of viral vaccines have been developed to protect these populations. Viral vaccines can include live viruses, attenuated viruses, subunits of viruses, and/or individual molecules to confer protection against a viral infection. Typically, the viral vaccines include at least a portion of the viral particle to induce the recipient of the viral vaccine to develop antibodies against the viral particle to prevent later infection. Viral vaccines have protected large segments of the world's population from infection by viruses. However, viral vaccines are frequently expensive and/or difficult to produce and process on large scales. Therefore, a need exists for apparatus and methods that improve various aspects of viral vaccine production.

Many viral vaccines can be needed cyclically, such as for example the influenza viral vaccines which are typically required annually before the flu season. Because production can take a considerable amount of time, it can be desirable to produce and store viral vaccine many months before it is needed. However, many viral vaccines can lose efficacy if stored in a usable formulation for a period of months. Therefore, many viral vaccines are dehydrated prior to storage to increase their shelf life and then resuspended prior to use.

Various processes have been used to dry viral vaccines. These processes are typically relatively inefficient and time consuming. The inefficiency and time make the end product more expensive. Further, current processes do not typically permit the continuous production of dried product. This can further increase the cost and time for production of a viral vaccine. Therefore, the need exists for apparatus and methods that may more quickly and efficiently prepare a viral vaccine for storage.

In one prior methodology, viral vaccines can be dehydrated by freeze drying. Freeze drying (also known as lyophilization) is a dehydration process that typically involves freezing the liquid viral vaccine and then reducing the surrounding pressure to sublimate the frozen water into the gas phase, which may be evacuated. After the frozen water has been sublimated and the water vapor evacuated, the end result is a viral vaccine in the dried state.

The process of producing dried viral vaccine by freeze drying typically includes several steps. The process typically begins by placing liquid viral vaccine within one or more vials, with the one or more vials being unsealed. The liquid viral vaccine within the one or more vials is then subjected to the freeze drying process resulting in one or more vials containing dried viral vaccine. After the freeze drying process is complete, the one or more vials may then be exposed to a sterilizing gas and then sealed in vacuum conditions. This results in one or more vials containing sterile dried viral vaccine. Alternatively, following freeze drying, the vials may be sealed and the sealed vials exposed to a radiation source for sterilization. Freeze drying viral vaccine may be a time consuming and energy inefficient process. Freeze drying is typically a batch type process where the liquid viral vaccine in groups of vials is subjected to the freeze drying process. Therefore, a need exists for more efficient methods for producing dried viral vaccine.

SUMMARY OF THE INVENTION

Methods and compositions in accordance with the present inventions may resolve many of the needs and shortcomings discussed above and will provide additional improvements and advantages, including faster and more efficient drying, larger batch sizes, higher viability and/or higher antigenic potency, longer shelf life in the dried state, and other properties.

The present invention is based on a variety surprising discovery that viral vaccines can be dried in a gas stream at very high temperatures, such as about 1000° F. and still retain viability and/or antigenic properties.

The present invention provides viral vaccines in the dried state produced by pulse combustion and methods for producing viral vaccines. In various aspects, the dried viral vaccine produced by pulse combustion may have one or more of the following properties: (1) particle size between about 1 and about 100 microns, (2) viral particle viability greater than about 30%, and preservation of antigenicity, (3) moisture content between about 0.5% and about 10%, (4) shelf life of greater than 12 months.

The viral vaccine in the dried state is formed by vaporizing the liquid medium in which the viral particles are suspended, using a gas stream. The gas stream has at least a certain velocity and/or a certain temperature selected to vaporize the liquid medium. The characteristics of the gas stream are selected to vaporize the liquid medium while retaining the ability of the viral particles to elicit an immunogenic response when administered as a vaccine.

The present invention may also provide methods for drying viral vaccine in the liquid state into viral vaccine in the dried state. The method may include the step of introducing the viral vaccine in the liquid state into gas stream. The methods may include the step of recovering the vaccine in a dried state from the gas stream.

In some aspects of the invention, the gas stream is a pulsed gas stream. The gas stream may have an inlet or first temperature and an outlet or second temperature. The first temperature of the gas stream may range from about 700° F. to about 1300° F., or from about 750° F. to about 1000° F. The second temperature of the gas stream may range from about 135° F. to about 250° F. The frequency of pulses of the gas stream may range from about 30 to 1000 Hertz.

In some embodiments, the viral vaccine introduced into the gas stream comprises an attenuated virus, killed viruses, viral components or combinations thereof.

The invention also provides a viral vaccine in a dried state, wherein the vaccine is dried by introducing the viral vaccine in the liquid state into gas stream and recovering the vaccine in a dried state from the gas stream. The gas stream may have an inlet or first temperature and an outlet or second temperature. The first temperature of the gas stream may range from about 700° F. to about 1300° F., or from about 750° F. to about 1000° F. The second temperature of the gas stream may range from about 135° F. to about 250° F. The frequency of pulses of the gas stream may range from about 30 to 1000 Hertz.

In some embodiments, the viral vaccine in a dried state comprises an attenuated virus, killed viruses, viral components or combinations thereof.

Other features and advantages of the inventions will become apparent from the following detailed description and from the claims.

BRIEF DESCRIPTION OF THE FIGURES

FIG. 3A illustrates by schematic diagram an embodiment of the packaging apparatus.

FIG. 3B illustrates a perspective view an embodiment of a package containing viral vaccine in the dried state.

FIG. 4 illustrates by schematic diagram an example of the drying of viral vaccine in the liquid state into viral vaccine in the dried state.

Figure 1:
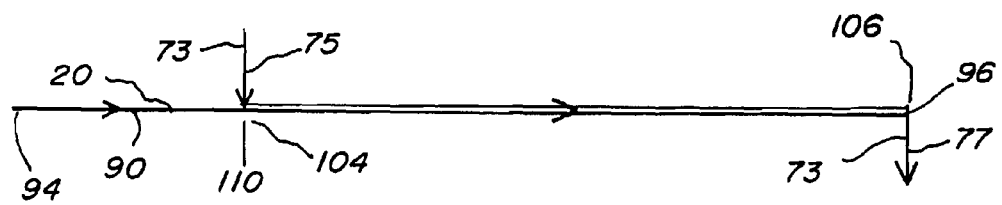
FIG. 1 illustrates by schematic diagram an example of the drying of viral vaccine in the liquid state.

All Figures are illustrated for ease of explanation of the basic teachings of the present inventions only; the extensions of the Figures with respect to number, position, order, relationship and dimensions will be explained or will be within the skill of the art after the following description has been read and understood. Further, the apparatus, materials and other operational parameters to conform to specific size, dimension, force, weight, strength, velocity, temperatures, flow and similar requirements will likewise be within the skill of the art after the following description has been read and understood.

Where used to describe the drawings, the terms "top," "bottom," "right," "left," "forward," "rear," "first," "second," "inside," "outside," and similar terms may be used, the terms should be understood to reference the structure and methods described in the specification and illustrated in the drawings as they generally correspond to their with the apparatus and methods in accordance with the present inventions as will be recognized by those skilled in the art upon review of the present disclosure.

DETAILED DESCRIPTION OF THE INVENTION

As used herein, the term, "animals" refers to all members of the kingdom animalia, including humans.

The present invention provides methods for removing liquid medium from viral vaccines. As used herein, viral vaccines include a liquid medium and one or more types of viral particles from one or more types of viruses. The invention also provides dried vaccines produced using a heated and/or pulsed gas stream. The apparatus typically includes a dryer to produce a gas stream to remove the liquid medium suspending the viral particles in the viral vaccine. In one aspect, the liquid medium is vaporized by a gas stream and the viral particles are left in a condition to elicit an immune response when administered as a vaccine. The gas stream may be heated and/or pulsed.

The Figures generally illustrate various exemplary embodiments of apparatus and methods including aspects of the present inventions. The particular exemplary embodiments illustrated in the figures have been chosen for ease of explanation and understanding of various aspects of the present inventions. These illustrated embodiments are not meant to limit the scope of coverage but instead to assist in understanding the context of the language used in this specification and the appended claims. Accordingly, variations of the apparatus and methods for dehydrating viral vaccines different from the illustrated embodiments may be encompassed by the appended claims.

Viruses for viral vaccines 73 are typically commercially produced by host cells supported in a growth medium. After a sufficient number of virus have been produced by the host cells, the virus is separated from the growth medium and remaining host cells and cell components. The virus may also be manipulated to inactivate it or to separate out desired portions or components of the virus to be administered to a patient. The virus or viral particles are then resuspended and may be concentrated in a liquid medium. The viral particles suspended in a liquid medium may constitute a viral vaccine 73.

The viral vaccine 73 is in a liquid state 75 when the viral particles 78 are suspended in the liquid medium. The viral vaccine 73 includes viral particle 78, which may include live or attenuated virus, portions or components of the virus and/or material derived from the virus configured to produce an immunologic response in the recipient to one or more pathogens. In some aspects, the viral particles 78 include killed virions. In other aspects, the viral particles 78 include live attenuated virions. In still other aspects, the viral particles 78 include various subunits of virions such as, for example, at least portions of the genome, at least portions of the capsid, or at least portions of the envelope, or combinations thereof. The viral particles 78 may be configured from virions in other ways and include other material or materials derived from the virions as would be recognized by those of skilled in the art in the art upon review of this disclosure.

The viral vaccine 73 in the liquid state 75 may be generally in a liquid form, or may be in the form of slurry, paste, or other viscous or non-Newtonian form. The viral vaccine 73 in the liquid state 75 may include various agglomerations, aggregations, non-homogeneities and/or clumps. The viral vaccine may also include adjuvants and other components known to the skilled artisan. When the liquid medium is water or otherwise aqueous, the moisture content of the viral vaccine 73 can be between 0.5% and 10%. In one embodiment, the moisture content is around 7% to 9% when the viral vaccine 73 is in the dried state 77. In accordance with aspects of the present invention, the liquid medium is removed from viral vaccine 73 by a gas stream 20. The removal of the liquid medium can allow for more prolonged storage of the viral vaccine 73. At least some of the ability to elicit an immune response of the viral vaccine 73 in the liquid state 75 is preserved when the viral vaccine 73 is dried from the liquid state 75 to the dried state 77 by the gas stream 20. Prior to administration, the viral vaccine 73 is typically resuspended. Upon administration, the resuspended viral vaccine is formulated to elicit an immunologic response in the recipient. The recipient may be a human being or an animal.

The viral vaccine 73 in the liquid state 75 may include water, and may include various acids, bases, and/or buffers to control the pH. Other non-aqueous solvents may also be included in the viral vaccine 73 in the liquid state 75 and various preservatives may be included in the viral vaccine 73 in the liquid state 75. In some embodiments, the viral vaccine 73 in the liquid state 75 may include a carrier material 79 with the carrier material 79 configured to form a portion of the viral vaccine 73 in the dried state 77 when the viral vaccine 73 in the liquid state 75 is dried into viral vaccine 73 generally in the dried state 77. The carrier material 79 may aid in the preservation of the viral particle 78 in the dried state 77. The carrier material 79 may provide bulk to the viral vaccine 73 in the dried state 77, and may assist in maintaining the activity of the viral vaccine 73 in the dried state 77. The carrier material 79 may be, for example, a sugar or combinations of sugars such as, without limitation, glucose, lactose, maltose, dextrose, fructose, mannose, xylose, ribose, cellobiose, raffinose, trehalose, maltodextrin or combinations thereof. The carrier material 79 may be protein or other carrier material, 79, such as, without limitation, 6-amino mannose, mannitol, sorbitol, glycerol, polyethylene glycols, maltotriose, dextran, maltodextrins, cellulose, aminoglycosides, amino acids, such as betaines, prolines, glycine arginine, lysine, alanine, sweet whey solids, albumin, polyvinyl alcohol, creatine, nonfat dry milk, polydextran, partially hydrolyzed starches, collagens, gelatins and combinations of materials as would be recognized by those of ordinary skill in the art upon review of this disclosure.

The activity of the viral vaccine 73 in the dried state 77 may be defined in various ways. As examples, the activity of the viral vaccine 73 may be defined as the ability of the viral vaccine 73 to induce an immunologic response in a recipient. In aspects wherein the viral particle 78 includes live attenuated virions, the activity of the viral vaccine 73 in the dried state 77 may be defined as the portion of virions in the viral vaccine 73 in the liquid state 75 that survive the drying of the viral vaccine 73 into the dried state 77. In aspects wherein the viral particle 78 includes subunits of the virions, the activity may be defined as the portion of the subunits unaltered in, for example, molecular structure and/or orientation after the viral vaccine 73 in the liquid state 75 is dried into the viral vaccine 73 in the dried state 77.

The viral vaccine 73 may be dried from the liquid state 75 to the dried state 77 by introducing the viral vaccine 73 generally in the liquid state 75 into a flowing gas stream 20 and recovering the viral vaccine 73 in the dried state 77 from the gas stream 20. The viral vaccine 73 is dried as the viral vaccine 73 is convected along portions of the flow path 90 by the gas stream 20. The viral vaccine 73 in the dried state 77 is drier than, and may be substantially drier than, the viral vaccine 73 in the liquid state 75. In some aspects, substantially all of the water may be removed from the viral vaccine 73 in the dried state 77, while, in other aspects, the viral vaccine 73 in the dried state 77 may retain some residual amount of water. The water content of the viral vaccine 73 in the dried state 77 may be less than 8%. Water, as used herein, may include, for example, water, water in combination with various acids, bases, and buffers, and water in combination with other solvents and additives, and other solvents and volatiles.

In some aspects, the gas stream 20 may consist generally of air and combustion products produced by the combustion of various solid, liquid, or gaseous fuels or combinations thereof. Examples of fuels would include propane, natural gas, and kerosene. In other aspects, the gas stream 20 may consist of heated air propelled by the release of compression. In various aspects, the gas stream 20 may include other gases or combinations of gases, which may be heated in various ways and configured to form the flowing gas stream 20, as would be recognized by those of ordinary skill in the art upon review of this disclosure.

In some aspects, the gas stream 20 may be characterized by a generally continuous flow. In other aspects, the gas stream 20 may be pulsed, and the pulses may have a frequency that may range from about 30 Hz to about 1,000 Hz. In various aspects, the gas stream 20 may include regions of high velocity flow, turbulence, and may include supersonic flows and shock waves. Pressures in the gas stream 20 may be about $2 \times 10^4$ Pa (gage) or more in various aspects. Sound pressures in the gas stream 20 may fall in the range of about 1100 dB to about 200 dB in various aspects. In various aspects, a swirl component may be induced into the flow of the gas stream 20.

The flow of the gas stream 20 defines a flow path 90 having a first end 94 and a second end 96 with the gas stream 20 flowing generally from the first end 94 to the second end 96. The first end 94 of the flow path 90 may be generally coincident with the location at which the gas stream 20 is generated. The second end 96 of the flow path 90 may be generally coincident with the region from which the viral vaccine 73 in the dried state 77 is recovered from the gas stream 20 and may be defined by various structures configured to recover the viral vaccine 73. The viral vaccine 73 in the liquid state 75 may be introduced into the gas stream 20 at an introduction location 110, with the introduction location 100 disposed along the flow path 90 generally between the first end 94 and the second end 96.

One or more passages 120, which may be defined by tubes, channels, pipes, or other structures, with each passage 120 having one or more passage outlets 122 adapted for the introduction of viral vaccine 73 into the gas stream 20 may be located in the flow path 90 between the first end 94 and the second end 96, and the location of the passage(s) 120 in the flow path 90 defines the introduction location 110. Viral vaccine 73 may be introduced into the gas stream 20 at the introduction location 110 through the passage(s) 120. Pumps, piping, valves, and other such structures may be provided in various aspects to convey the viral vaccine to the passage(s) 120 for introduction into the gas stream 20 at the introduction location 110 as would be recognized by those of ordinary skill in the art upon review of this disclosure.

The temperature of the gas stream 20 may be 2,300° F. or more generally proximate the first end 94 of the gas stream 20, which may be excessive for drying viral vaccine 73. Accordingly, the temperature of the gas stream 20 may be controlled, in various aspects, to provide a specific first temperature 104 generally proximate the introduction location 110 and a specific second temperature 106 generally proximate the second end 96 of the flow path 90. The temperature of the gas stream 20 may be controlled in various aspects to control the first temperature 104 of the gas stream 20 generally proximate the first end 94 of the flow path 90 where the viral vaccine 73 in the liquid state 75 may be introduced into the gas stream 20. The temperature of the gas stream 20 may be controlled in various aspects to control the second temperature 106 of the gas stream 20 generally proximate the second end 96 of the flow path 90 where the viral vaccine 73 in the dried state 77 may be recovered from the gas stream 20.

For example, one or more gas flows may be combined with the gas stream 20 as the gas stream 20 flows along the flow path 90 to control, at least in part, the first temperature 104 of the gas stream 20 at introduction location 110. The one or more gas flows combined with the gas stream 20 may control, at least in part, the temperature at the second end 96 of the flow path 90. The one or more gas flows combined with the gas stream 20 may control, at least in part, the temperature variation between the first temperature 104 and the second temperature 106. In various aspects, one or more gas flows may be combined with the gas stream 20 to provide for the uptake of water vapor and/or for other purposes as would be recognized by those of ordinary skill in the art upon review of this disclosure. In various aspects, conditions at the first end 94 of the flow path 90 may be adjusted in order to achieve a specific first temperature 104 and/or specific second temperature 106.

The first temperature 104 and/or the second temperature 106 may be chosen depending upon the nature of the viral vaccine 73 to be introduced into the gas stream 20 in order to be dried into the dried state 77. For example, in various aspects, the first temperature 104 may be about 1,000° F. while the second temperature 106 may be about 170° F.

The viral vaccine 73 may be introduced into the gas stream 20 at the introduction location 110 to be exposed to the temperature of the gas stream 20 while being conveyed by the gas stream 20 from the introduction location 110 to the second end 96 of the flow path 90. The viral vaccine 73 may be exposed to the temperature of the gas stream 20 for an exposure time that may be on the order of fractions of a second, and, in some aspects, on the order of a millisecond or less. The temperature of the gas stream 20 may cause water associated with the viral vaccine 73 to flash into the vapor phase, while the latent heat of vaporization of the water in combination with the exposure time may keep the viral vaccine 73 generally cool thereby protecting the viral vaccine 73 from the temperature of gas stream 20. Turbulence, high velocities, and/or shock waves in the gas stream 20 may strip water from the viral vaccine 73 and may otherwise increase the rate of evaporation of water from the viral vaccine 73 by various mechanisms. The latent heat of evaporation of the water may also cool the gas stream 20, at least in part, from the first temperature 104 to the second temperature 106, so that the water content of the viral vaccine 73 in the wet state 75 may, in some aspects, control the second temperature 106 and may control the temperature variation between the first temperature 104 and the second temperature 106, at least in part. The rate at which viral vaccine 73 in the liquid state 75 is fed into the gas stream 20 may control the first temperature 94, may control the second temperature 96, and may control the form of the temperature gradient between the first temperature 94 and the second temperature 96.

A collector 60 may be positioned about the second end 96 of the flow path 90 to recover the viral vaccine 73 generally in the dried state 77 from the gas stream 20, and the collector 60 may generally define the second end 96 of the flow path 90. The collector 60 may be a cyclone, baghouse, screen or series of screens, filter(s), or similar, or combinations thereof configured to capture the viral vaccine 73 generally in the dried state 77 from the gas stream 20 as would be recognized by those of ordinary skill in the art upon review of this disclosure.

A packaging apparatus 165, in various aspects, may be configured to cooperate with the collector 60. One or more packages 170 including vials, ampoules, bottles, gas impermeable packages, and other sealable containers and including any necessary sealing materials such as stoppers, rubber and/or synthetic membranes, metal and/or plastic bands, adhesives, and suchlike may be provided as would be recognized by those of ordinary skill in the art upon review of this disclosure, with the package 170 defining a package interior 172. The packaging apparatus 165 is configured to receive viral vaccine 73 in the dried state 77 from the collector 60 and to place the viral vaccine 73 in the dried state 77 into the package interior 172 of one or more packages 170. Various material handling and storage mechanisms for the manipulation and/or storage of viral vaccine 73 in the dried state 77 may be included with the packaging apparatus 165 as would be recognized by those of ordinary skill in the art upon review of this disclosure.

Aliquots of the viral vaccine 73 in the dried state 77 may be placed into the package interior 172 of the one or more packages 170 in such amounts that, when resuspended by the addition of liquid such as sterile buffered saline solution into the package interior 172 of the package 170, the now resuspended viral vaccine 73 achieves a concentration of viral particle 78 appropriate for the inoculation of one or more recipients.

The packaging apparatus 165 may be configured to seal the package 170 following placement of the viral vaccine 73 within the package interior 172, and the packaging apparatus 165 may be configured to sterilize the package interior 172 following placement of the viral vaccine 73 in the dried state 77 within the package interior 172.

In some aspects, the packaging apparatus 165 may seal the viral vaccine 73 in the dried state 77 within the package interior 172 of the one or more packages 170. Air and/or other gasses may be evacuated from the package interior 172 so that the viral vaccine 73 in the dried state 77 is sealed within the package interior 172 under substantially vacuum conditions. In some aspects, an inert gas could be placed within the sealed package interior 172. The one or more packages 170 may then be irradiated by, for example, gamma radiation from a gamma source 180 to sterilize the package interior 172. Alternatively, the sealed packages 170 may be Tyndallized by being subjected to repeated heating and cooling to sterilize the package interior 172.

In other aspects, the packaging apparatus 165 may place the viral vaccine 73 in the dried state 77 within the package interior 172 of the one or more packages 170 with the one or more packages 170 unsealed. The package interior 172 of the one or more packages 170 may then be exposed to a sterilizing gas such as ethylene dioxide may then be introduced into the package interior 172. After a suitable exposure time, the sterilizing gas may be evacuated from the package interior 172 of the one or more packages 170 and the one or more packages 170 sealed. In some aspects, the package interior 172 may be repetitively exposed to the sterilizing gas prior to the sealing of the package 170. Other sterilization techniques could also be employed in various aspects as would be recognized by one of ordinary skill in the art upon review of this disclosure.

In some aspects, the gas stream 20 may be generated by a pulse combustion dryer 30. Examples of pulse combustion dryers 30 are described in U.S. Pat. Nos. 3,462,995, 4,708,159, 4819,873, and 4,941,820. The pulse combustion dryer 30 may include a combustor 31 that defines a combustion chamber 32, and a tailpipe 40 that defines a tailpipe passage 42 having a first tailpipe passage end 44 and a second tailpipe passage end 46. The tailpipe passage 42 is in fluid communication with the combustion chamber 32 through the first tailpipe passage end 44.

The pulse combustion dryer 30, in some aspects, may include a drying chamber 50 that defines a drying chamber passage 52 having a first drying chamber passage end 54, a second drying chamber passage end 56, and centerline 153. The first drying chamber passage end 54 of the drying chamber 50 may be disposed with respect to the second tailpipe passage end 46 of the tailpipe 40 so that the drying chamber passage 52 is in fluid communication with the tailpipe passage 42, and, thence, in fluid communication with the combustion chamber 32. The combustor 31, tailpipe 40, and drying chamber 50 may be disposed with respect to one another in a variety of ways and may assume a variety of orientations with respect to the vertical that would be readily recognized by those of ordinary skill in the art upon review of this disclosure.

Combustion air 86 and fuel 84 may be admitted into the combustion chamber 32, and the resulting fuel-air mixture ignited periodically to provide the gas stream 20 in the form of a series of pulses of air mixed with heated combustion products. Combustion of the fuel-air mixture may be generally complete so that the heated combustion products would consist largely of carbon dioxide and water vapor. The gas stream 20 may flow from the combustion chamber 32, thru the tailpipe passage 42 from the first tailpipe passage end 44 to the second tailpipe passage end 46. In aspects that include the drying chamber 50, the gas stream 20 may be communicated from the tailpipe passage 42 into the drying chamber passage 52 generally proximate the first drying chamber passage end 54, and the gas stream 20 may flow through the drying chamber passage 52 generally from the first drying chamber passage end 54 to the second drying chamber passage end 56. Thus, the flow path 90 of the gas stream 20 includes the combustion chamber 32, the tailpipe passage 42, and, in aspects that include the drying chamber 50, the flow path 90 also generally includes the drying chamber passage 52. The first end 94 of the flow path 90 may be generally coincident with the combustion chamber 32.

In aspects wherein the gas stream 20 is generated by the pulse combustion dryer 30, the collector 60 may be disposed generally proximate the tailpipe passage second end 96 or, in aspects that include the drying chamber 50, generally proximate the second drying chamber passage end 56 to recover the viral vaccine 73 in the dried state 77. As would be understood by those of ordinary skill in the art upon review of this disclosure, the collector 60 may be disposed in other ways with respect to the drying chamber 50 to recover the viral vaccine 73 in the dried state 77 from the second end 96 of the flow path 90 of the gas stream 20.

The viral vaccine 73 generally in the liquid state 75 may be introduced into the flow path 90 of the gas stream 20 at the introduction location 110. In various aspects, the introduction location 110 may be within the tailpipe passage 42 or within the drying chamber passage 52. The viral vaccine 73 may be entrained in the gas stream 20 generally at the introduction location 110 and dried while being conveyed by the gas stream 20 along the portion of the flow path 90 from the introduction location 110 to the second end 96 of the flow path 90. The viral vaccine 73 in the dried state 77 may be recovered at the second end 96 of the flow path 90 of the gas stream 20 by the collector 60.

The viral vaccine 73 in the liquid state 75 may be introduced into the gas stream 20 at the introduction location 110 from one or more passages 120 through one or more passage outlets 122 defined by the one or more passages 120 disposed about the gas stream 20 at the introduction location 110 for that purpose. The viral vaccine 73 may pass through the one or more passages 120 into the gas stream 20 by gravity feed and/or by the application of pressures, which may be quite minimal. Pressure pulses in the gas stream 20 may aid in drawing the viral vaccine 73 through the passage 120 and into the gas stream 20. Accordingly, the shear forces that the viral vaccine 73 is subjected to while passing through the passage 120 may be generally small or negligible. In various aspects, the rate at which viral vaccine 73 is fed into the gas stream 20 may be controllable.

In some aspects, nozzles, sprayers, or similar may be appended to the passage 120 to disperse the viral vaccine 73 from the passage outlet 122 into the gas stream 20. However, this may not be necessary, as the violence of the flow of the gas stream 20 may be sufficient to disperse the viral vaccine 73 including the dispersal of any agglomerations, aggregations, non-homogeneities and/or clumps of materials such as the viral particle 78. The shock waves and/or turbulence in the gas stream 20 may disperse the viral vaccine. Sound waves in the gas stream 20 may sonicate the viral vaccine 73, which may aid in the dispersal of the viral vaccine 73 into the gas stream 20. Pressure pulses in the gas stream 20 may also aid in the dispersal of the viral vaccine 73 into the gas stream 20.

FIG. 1 illustrates by schematic diagram the methods of drying the viral vaccine 73 in the liquid state 75 into viral vaccine 73 in the dried state 75 using the gas stream 20. This Figure depicts the gas stream 20 flowing along flow path 90 from the first end 94 to the second end 96. The viral vaccine 73 in the liquid state 75 is introduced into the gas stream 20 at introduction location 110 as illustrated. The viral vaccine 73 is dried by the gas stream 20 while being convected by the gas stream 20 from the introduction location 110 to the second end 96 of the flow path 90. The viral vaccine 73 in the dried state 77 is recovered from the gas stream 20 proximate the second end 96 of the flow path 90, the location or locations at which the viral vaccine 73 in the dried state 77 is recovered from the gas stream 20 generally defining the second end 94.

Figure 2A:
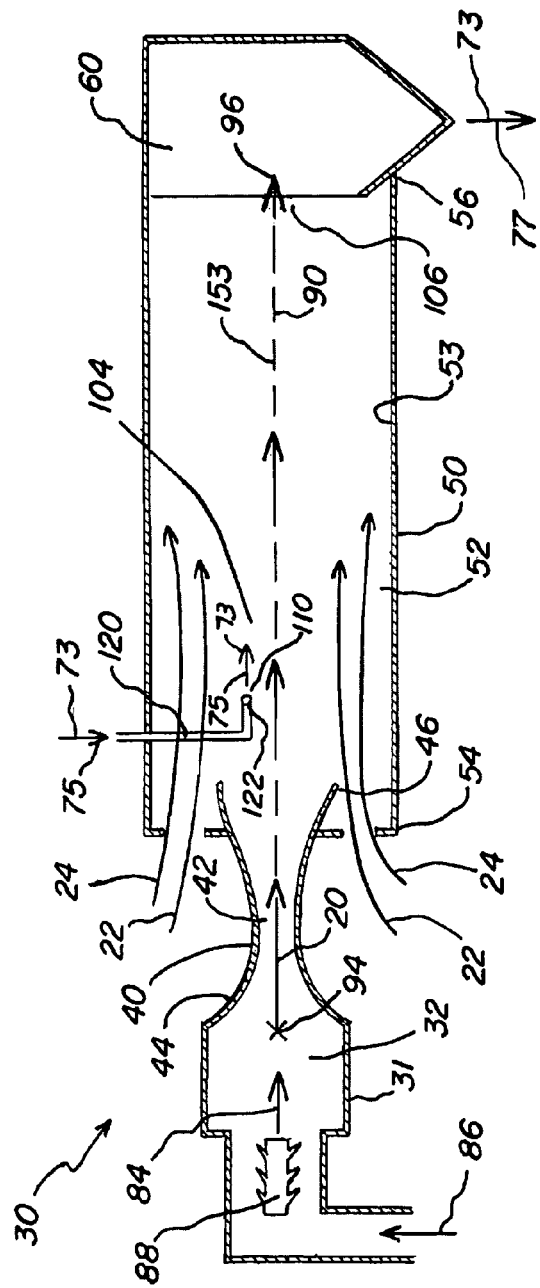
FIG. 2A illustrates by schematic diagram an embodiment of the pulse combustion dryer.

An embodiment of the pulse combustion drier 30 is generally illustrated in FIG. 2A. The embodiment of FIG. 2A includes the combustor 31, the tailpipe 40, and the drying chamber 50. The combustion chamber 31 fluidly communicates with the tailpipe passage 42 through the first tailpipe passage end 44. The tailpipe 40 is disposed with respect to the drying chamber 50 such that the tailpipe passage 42 fluidly communicates through the second tailpipe passage end 46 into the drying chamber passage 52 generally proximate the first drying chamber passage end 54, as illustrated. The drying chamber passage 52 fluidly communicates with the collector 60 through the second drying chamber passage end 56, in this embodiment. In other embodiments, the collector 60 could be otherwise disposed with respect to the drying chamber 50. For example, at least a portion of the collector 60 could be positioned within a portion of the drying chamber passage 52 generally proximate the second drying chamber passage end 56.

In the embodiment illustrated in FIG. 2A, the gas stream 20 is generated within the pulse combustion dryer 30 and the viral vaccine 73 in the wet state 75 is dried into the viral vaccine in the dry state 75 by the pulse combustion dryer 30. Fuel 84 and combustion air 86 are admitted into the combustion chamber 32 defined by the combustor 31 to be ignited periodically in order to produce the gas stream 20. An air valve 88 may be disposed in the path of the combustion air 88 to admit combustion air 88 into the combustion chamber 32 while generally preventing backflows of the gas stream 20, as illustrated. As illustrate in FIG. 2A, the flow of the gas stream 20 from the combustion chamber 32, through the tailpipe passage 42, through the drying chamber passage 52 and into the collector 69 defines the flow path 90. The first end 94 of the flow path 90 is generally within the combustion chamber 32, and the second end 96 of the flow path 90 is generally proximate the collector 60 which is disposed about the second drying chamber passage end 56 of the drying chamber 50 in the embodiment illustrated in FIG. 2A.

Viral vaccine 73 generally in the liquid state 75 may be introduced into the gas stream 20 at the introduction location 110 through the passage outlet 122 defined by passage 120 in the embodiment illustrated in FIG. 2A. In this embodiment, a portion of the tailpipe 40 extends into the drying chamber passage 52 of the drying chamber 50. The introduction location 110, in this embodiment, is within the drying chamber passage 52 generally proximate the tailpipe passage second end 46 and generally proximate the first drying chamber passage end 54. The passage 120 is disposed within the drying chamber passage 52 to introduce the viral vaccine into the gas stream 20 generally proximate the centerline 153 of the drying chamber passage 52 in the embodiment of FIG. 2A.

In other embodiments, a plurality of passages 120 may be provided. One or more tubes may be disposed within the drying chamber passage 42, in some embodiments, to introduce the viral vaccine 73 into the gas stream 20 at an off-set from the centerline 153. For example, a plurality of passages 120 may be disposed circumferentially within the drying chamber passage 42 with each passage 120 of the plurality of passages 120 positioned to introduce the viral vaccine 73 into the gas stream 20 at a constant radial location with respect to the centerline 153.

As illustrated in FIG. 2A, the viral vaccine 73 introduced into the gas stream 20 through the passage outlet 122 may be entrained into the gas stream 20 to be dried from the liquid state 75 to the dried state 77. The viral vaccine 73 generally in the dried state 77 may then be recovered from the gas stream 20 by the collector 60. The collector 60 is positioned proximate the second drying chamber passage end 56 and generally defines the second end 96 of the flow path 90, in this illustrated embodiment.

As illustrated in FIG. 2A, one or more additional airflows may be admitted into the drying chamber passage 52 in various embodiments of the pulse combustion dryer 30. In the embodiment of FIG. 2A, quench air 22 may be admitted into the drying chamber passage 52 generally proximate the first drying chamber end 54 to control the temperature of the gas stream 20 within the drying chamber passage 52. The quantity of quench air 22 admitted into the drying chamber passage 52 may be regulated in order to control the temperature of the gas stream 20 including the first temperature 104 and the second temperature 106. In this embodiment, dilution air 24 may also introduced into the drying chamber passage 52 generally proximate the first drying chamber passage end 54 to provide thermodynamic space for the uptake of water evaporated from the viral vaccine 73 in order to prevent water condensation and/or saturation conditions in the drying chamber passage 52 and/or in the collector 60. The quantity of dilution air 24 admitted into the drying chamber passage 52 may be regulated in various embodiments.

In the embodiment illustrated in FIG. 2A, the gas stream 20 may pass through a core region 155 generally proximate the centerline 153 of the drying chamber passage 52. The dilution air 24 may pass through the wall region 159 of the drying chamber passage 52 which is the portion of the drying chamber passage 52 generally proximate the inner wall 53 of the drying chamber 50. The quench air 22 may pass through an intermediate region 157 which is intermediate between the wall region 159 and the core region 155.

Viral vaccine 73 may be introduced into the gas stream 20 passing though the core region 155. The quench air 22 and/or the dilution air 24 may prevent or at least diminish contact between the viral vaccine 73 and the inner wall 53 of the drying chamber 50 as the viral vaccine 73 is convected through the drying chamber passage 42 by the gas stream 20 in order to generally reduce or eliminate deposition of viral vaccine 73 onto the inner wall 53.

Figure 2B:
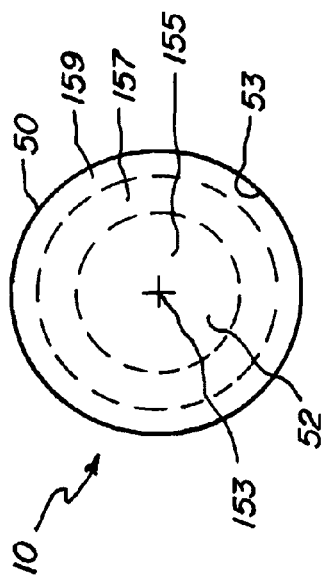
FIG. 2B illustrates by schematic diagram a cross-section of an embodiment of the drying chamber.

FIG. 2B illustrates a cross-section of the drying chamber 50. As illustrated, the drying chamber 50 defines a drying chamber passage 52 having a substantially circular cross-section. In this embodiment, the flows of the gas stream 20, the quench air 22, and the dilution air 24 through the drying chamber passage 52 generally define three regions within the drying chamber passage. These regions include the core region 155 generally proximate the centerline 153 through which the gas stream 20 generally passes, the intermediate region 155 through which the quench air 22 generally passes, and the wall region 159 through which the dilution air 24 generally passes. The pulse combustion dryer 30 may be configured to regulate the amount of quench air 22 and/or the amount of dilution air 24 admitted into the drying chamber passage 52 in order to regulate temperature and other conditions within the drying chamber passage 52. In other embodiments, one or more airstreams could be introduced into the drying chamber passage 52 at various locations about the drying chamber passage 52 to cool the gas stream 20, provide thermodynamic space for evaporation, or for other purposes as would be understood by those of ordinary skill in the art upon review of this disclosure.

The gas stream 20 has a first temperature 104 generally proximate the introduction location 110, as illustrated in FIG. 2A. The gas stream 20 has a second temperature 106 generally proximate the second end 96 of the flow path 90 of the gas stream 20, as illustrated. In various embodiments, the pulse combustion dryer 30 may be configured to regulate the amount of additional gas flows such as the quench air 22 and the dilution air 24 admitted into the gas stream 20 to regulate the temperature. In various embodiments, the fuel admitted into the combustion chamber 32 may be controlled, the pulse rate of the pulse combustion dryer 30 may be regulated, and/or the pulse combustion dryer 30 may be configured and/or controlled in other ways to regulate the temperature of the gas stream 20 including the first temperature 104 and the second temperature 106 as would be recognized by those of ordinary skill in the art upon review of this disclosure.

In the schematic diagram of FIG. 3A, the collector 60 recovers the viral vaccine 73 in the dried state 77 from the gas stream 20. The collector 60, as illustrated, cooperates with the packaging apparatus 165 to seal the viral vaccine 73 in the dried state 77 within the package interior 172 of one or more packages 170. A gamma source 180 is provided in this embodiment to irradiate the package interior 172 and viral vaccine 73 in the dried state 77 for sterilization in this embodiment. FIG. 3B illustrates an embodiment of the package 170 with viral vaccine 73 in the dried state 77 sealed within the package interior 172.

FIG. 4 illustrates schematically an embodiment of the combination of viral particle 78 and carrier material 79 to form the viral vaccine 73 in the dried state 77. As illustrated, the viral vaccine 73 in the liquid state 77 includes the viral particle 78 and the carrier material 79 suspended in water. Upon drying, the viral particle 78 may be interposed with the carrier material 79, as illustrated. Drying the viral vaccine 73 in the gas stream 20 may result in the formation of generally spherical particles of viral vaccine 73 in the dried state 77, as illustrated.

EXAMPLES

A further understanding may be obtained by reference to certain specific examples, which are provided herein for the purpose of illustration only and are not intended to be limiting unless otherwise specified.

Example 1

In example 1, viral particle 78 in the form of purified attenuated live virus is suspended in buffered aqueous solution with an added carrier material 79 to form the viral vaccine 73 in the liquid state 75. The concentration of viral particle 78 (i.e. attenuated live virus particles) is about 0.1% to about 5.0% solids by weight with a preferred concentration of about 1.5% to about 3.0%. The pH of the buffered solution is between about 5.5 and about 8.5, and in some embodiments has a pH range of about 6.5 to about 7.5. The buffer concentration is between about 10 mM and about 200 mM, and in some embodiments has a concentration of about 20 mM to about 70 mM, and the buffer is compatible with an injectable medical solution such as, for example, potassium phosphate buffer. The concentration of carrier material 79 is about 2.5% to about 30% solids by weight, and in some embodiments has a concentration of about 10.0% to about 20% solids by weight. The carrier material 79 acts to bulk up the viral vaccine 73 in the dried state 77 and to protect the viral particle 78 from damage during the drying process. The carrier material 79 is biologically compatible with use in an injectable medical solution, for example, sugar such as glucose, lactose, or trehalose, or other suitable material.

The viral vaccine 73 in the liquid state 75 including the buffered aqueous solution of attenuated live virus particles, buffer and carrier is dried using a pulse combustion spray drier (for example a Pulse Combustion Systems Model P-0.3) in this example. The viral vaccine 73 in the liquid state 75 is conveyed to the drying chamber 50 using a sanitary system of pumps and hoses where the viral vaccine 73 in the liquid state 75 is introduced into the gas stream 20 within the pulse combustion dryer 30 at the introduction location 110 through one or more passages 120 adapted for that purpose. The first temperature 104 of the gas stream 20 generally proximate the introduction location 110 is between about 700° F. and about 1300° F., and in some embodiments has a temperature range of 750° F. and 850° F. The second temperature 106 generally proximate the second drying chamber passage end 56 is between about 135° F. and about 250° F., and in some embodiments has a range of about 140° F. to about 180° F. The feed rate at which the viral vaccine in the liquid state 75 is introduced into the gas stream is adjusted to maintain the second temperature 106 within the desired range.

The viral vaccine 73 in the dried state 77 containing live attenuated virus with buffer and carrier is conveyed from the second drying chamber passage end 56 pneumatically to the collector 60 in example 1. The collector 60, in example 1, is a cyclone precipitator, a sanitary bag house, or other appropriate method for capturing the viral vaccine 73 in the dried state 77 in a sanitary fashion. The viral vaccine 73 in the dried state 77 has a particle size of between about 1 and about 100 microns, and in some embodiments ranges from about 1 to about 20 microns. The moisture content of the powder is between about 0.5% and about 10%, and in some embodiments ranges from about 0.5% to about 3.0%. The activity of the viral vaccine 73 in the dried state 77 is defined, in this example, as the viral particle viability in the viral vaccine 73 in the dried state 77, which is generally greater than 30%, and in some embodiments is generally greater than 90% of the viability of the viral particles in the liquid state before drying.

In example 1, the viral vaccine 73 in the dried state 77 is portioned into sanitary packages 170 sized to serve the end user. Material intended for use in mass inoculation programs will be in larger packages 170 than material intended for individual inoculations. The packages 170 may be sealed and crimped before being subjected to sterilization by irradiation, for example gamma irradiation. Alternatively the packages 170 may be partially stoppered and subject to gas sterilization, for example using ethylene dioxide gas, before being sealed and crimped.

In example 1, the end product is a vial 170 containing sterile viral vaccine 73 in the dried state 77 suitable for use in human and/or animal health applications.

Example 2

Purified viral particles 78 including inactivated virus and constituent parts are suspended in buffered aqueous solution with an added carrier material 79. The concentration of virus material is 0.1% to 5.0% solids by weight, and in some embodiments have a concentration of 1.5% to 3.0%. The pH of the buffered solution is between 5.5 and 8.5, and in some embodiments, is between 6.5 to 7.5. The buffer concentration is between 10 mM and 200 mM with, and in some embodiments has a concentration of 20 mM to 70 mM. The buffer used is compatible with an injectable medical solution, for example potassium phosphate buffer. The concentration of carrier material 79 is 2.5% to 30% solids by weight with a preferred concentration of 10.0% to 20%. The carrier material 79 acts to bulk up the final viral vaccine 73 in the dried state 77 and to protect the virus particles 78 from damage during the drying process. The carrier material 79 is biologically compatible with use in an injectable medical solution, for example, glucose, lactose, trehalose, or other suitable material.

The viral vaccine 73 in the liquid state 75 is conveyed to the drying chamber 50 using a sanitary system of pumps and hoses where the viral vaccine 73 in the liquid state 75 is introduced into the gas stream 20 within the pulse combustion dryer 30 at the introduction location 110 through one or more passages 120 adapted for that purpose. The temperature of gas stream 20 generally proximate the introduction location 110 is between about 700° F. and about 1300° F., and in some embodiments is between about 750° F. and 850° F. The second temperature 106 generally proximate the second drying chamber passage end 56 is between about 135° F. and 250° F., and in some embodiments has a range of about 140° F. to 180° F. The feed rate of the viral vaccine 73 in the liquid state 75 into the gas stream 20 is adjusted to maintain the second temperature 106 within the desired range.

The viral vaccine 73 in the dried state 77 containing virus particles 78 that include inactivated virus and constituent parts with buffer and carrier is conveyed pneumatically from the second drying chamber passage end 56 to the collector 60. The collector 60 in example 2 is a cyclone precipitator, a sanitary bag house, or other appropriate method for capturing the dried powdered material in a sanitary fashion. The viral vaccine 73 in the dried state 77 has a particle size of between 1 and 100 microns, and in some embodiments the particle size is between about 1 and 20 microns. The moisture content of the viral vaccine 73 in the dried state 77 is between about 0.5% and 10%, and in some embodiments ranges from about 0.5% to 3.0%. The activity of the viral vaccine 73 in the dried state 77 is defined, in this example, as the antigenic potency of the virus particles 78. In this example, the virus particles 78 retain at least about 30% of their antigenic potency, and in some embodiments have greater than about 90% of the antigenic potency as they had in the liquid state before drying In example 2, the viral vaccine 73 in the dried state 77 is portioned into sanitary packages 170 sized to serve the end user. Material intended for use in mass inoculation programs will be in larger vials than material intended for individual inoculations. The vials may be sealed and crimped before being subjected to sterilization by irradiation, for example gamma irradiation. Alternatively they may be partially stoppered and subject to gas sterilization, for example using ethylene dioxide gas, before being sealed and crimped. The end product is a sterile vaccine suitable for use in human and animal health application.

The foregoing discussion discloses and describes merely exemplary embodiments. Upon review of the specification, one of ordinary skill in the art will readily recognize from such discussion, and from the accompanying figures and claims, that various changes, modifications and variations can be made therein without departing from the spirit and scope of the invention as defined in the following claims.

All publications, patent publications and applications mentioned in this specification are herein incorporated by reference in their entireties to the same extent as if each individual publication or patent application was specifically and individually indicated to be incorporated by reference.

What is claimed is:

1. A method for drying a viral vaccine, comprising:
introducing a viral vaccine in a liquid state into a pulsed gas stream, the gas stream flowing from a first end to a second end; and
recovering the viral vaccine in a dried state from the gas stream wherein the gas stream first end has a first temperature and the gas stream second end has a second temperature, the first temperature being larger than the second temperature.

2. The method of claim 1, wherein first temperature of the gas stream ranges from about 700° F. to about 1300° F.

3. The method of claim 1, wherein the first temperature of the gas stream ranges from about 750° F. to about 1000° F.

4. The method of claim 2, wherein the frequency of pulses range from about 30 to 1000 Hertz.

5. The method of claim 4, wherein the second temperature of the gas stream ranges from about 135° F. to about 250° F.

6. The method of claim 5, wherein the viral vaccine comprises an attenuated virus.

7. The method of claim 5, wherein the viral vaccine comprises an attenuated virus, killed viruses, viral components, or combinations thereof.

8. The method of claim 1, wherein the pulsed gas stream is a continuous gas stream.

9. The method of claim 1, wherein the pulsed gas stream includes one or more regions of high velocity flow, turbulence, supersonic flows and supersonic shock waves.

10. The method of claim 1, wherein the pulsed gas stream comprises one or more of air and combustion products.

11. The method of claim 10, wherein the combustion products are produced by the combustion of solid, liquid, gaseous fuels or a combination thereof.

12. The method of claim of claim 1, wherein liquid state comprises a liquid, slurry, paste or other viscous or non-Newtonian form.

13. The method of claim 1, wherein the dried state comprises a moisture content less than about 8%.

14. The method of claim 1, wherein the dried state comprises a moisture content between about 7% and about 9%.

15. A method of drying a viral vaccine, comprising:
introducing a viral vaccine in a liquid state into a gas stream the gas stream flowing from a first end to a second end; and
recovering the viral vaccine in a dried state from the gas stream;
wherein the gas stream first end has a first temperature between about 700° F. to about 1300° F. and the gas stream second end has a second temperature is between about 135° F. to about 250° F.

* * * * *